United States Patent [19]

Lansink-Rotgerink et al.

[11] Patent Number: 5,959,164
[45] Date of Patent: Sep. 28, 1999

[54] USE OF CATALYSTS BASED ON CATALYST SUPPORTS CONTAINING SILICON DIOXIDE FOR CATALYTIC REACTIONS UNDER HYDROTHERMAL CONDITIONS

[75] Inventors: H. G. J. Lansink-Rotgerink, Glattbach; Heike Riedemann, Moembris; Thomas Tacke, Friedrichsdorf; Helmfried Krause, Rodenbach; Andreas Freund, Kleinostheim; Roland Burmeister, Geiselbach; Peter Panster, Rodenbach, all of Germany

[73] Assignee: Degussa Hüls Aktiengesellschaft, Frankfurt, Germany

[21] Appl. No.: 08/806,715

[22] Filed: Feb. 27, 1997

Related U.S. Application Data

[63] Continuation-in-part of application No. 08/589,256, Jan. 23, 1996, Pat. No. 5,808,136.

[30] Foreign Application Priority Data

Feb. 28, 1996 [DE] Germany .......................... 196 07 494

[51] Int. Cl.⁶ .............................. C07C 29/04; B01J 21/06
[52] U.S. Cl. ................................................ 568/896; 502/63
[58] Field of Search ................................ 568/896; 502/63

[56] References Cited

U.S. PATENT DOCUMENTS

| | | | |
|---|---|---|---|
| 3,311,568 | 3/1967 | Klimenko | 252/435 |
| 5,208,195 | 5/1993 | Schlueter et al. | 502/63 |
| 5,349,096 | 9/1994 | Cockman et al. | 568/896 |

FOREIGN PATENT DOCUMENTS

| | | |
|---|---|---|
| 0 393 356 A1 | 10/1990 | European Pat. Off. . |
| 0 503 229 A1 | 9/1992 | European Pat. Off. . |
| 0 578 441 A2 | 1/1994 | European Pat. Off. . |

*Primary Examiner*—John Kight
*Assistant Examiner*—Charanjit S. Aulakh
*Attorney, Agent, or Firm*—Smith, Gambrell & Russell

[57] ABSTRACT

The use of modified silicon dioxide as a catalyst support in catalytic reactions under hydrothermal conditions is described. The pore structure of the supports may be stabilized against hydrothermal reaction conditions by impregnating the catalyst supports with elements of Group IVB of the Periodic Tube of Elements.

16 Claims, 2 Drawing Sheets

_US. Pat. No. 5,959,164_

USE OF CATALYSTS BASED ON CATALYST SUPPORTS CONTAINING SILICON DIOXIDE FOR CATALYTIC REACTIONS UNDER HYDROTHERMAL CONDITIONS

This is a continuation-in-part application of U.S. application Ser. No. 08/589,256, filed Jan. 23, 1996, which has issued into U.S. Pat. No. 5,808,136 on Sep. 15, 1998, which is relied on and incorporated in its entirety herein by reference.

INTRODUCTION AND BACKGROUND

This present invention relates to the use of catalysts, which have an active component on a catalyst support containing silicon dioxide, for catalytic reactions under hydrothermal conditions. Hydrothermal conditions prevail in chemical reactions in aqueous systems when the temperature is above the boiling point of water and pressure is above standard pressure.

A typical reaction under hydrothermal conditions is the hydration of olefins to yield the corresponding alcohols in the presence of phosphoric acid as the catalyst or active component on a catalyst support containing silicon dioxide.

Such a process is described, for example, in EP 0 578 441 A2. In that process, water and ethylene are reacted at temperatures of between 225 and 280° C. and pressures of between 20 and 240 bar to yield ethanol. A molar ratio of water to ethylene in the range from 0.15 to 0.5 is used in this reaction. Catalyst loading, measured in grams of water/ethylene mixture per minute per milliliter of catalyst, may be selected within the range from 0.01 to 0.1 g/(min×ml). Diethyl ether is formed as a secondary product in that reaction. Isopropanol is produced by hydrating propylene under similar conditions to those stated above, but at a slightly lower temperature in the range between 180 and 225° C. The byproduct in this reaction is n-propanol.

The catalyst support used for the active component phosphoric acid in EP 0 578 441 A2 comprises pellets of synthetic silicon dioxide having a high crush strength, high porosity and few metallic contaminants. The purpose of the pores of the support is to accommodate the active component. Pore volume is thus preferably greater than 0.8 ml/g. Average pore radius prior to use in the hydration process is in the range between 1 and 50 nm.

In order to achieve optimum hydration performance, EP 0 578 441 A2 specifies a silicon dioxide content of the support of at least 99 wt. % with below 1 wt. %, preferably below 0.3 wt. % of contaminants.

Catalysts undergo aging during operation, which is discernible by a reduction in activity and/or selectivity. Deactivation is frequently due to a reduction in the specific surface area of the support brought about by elevated temperatures. Specific surface area in the context of this application means the BET surface according to Brunauer, Emmett and Teller determined by nitrogen adsorption according to DIN 66 132.

The specific surface area of a support is closely related to its pore structure. Moreover, solids having a high surface area usually have a completely or predominantly amorphous structure, which has a strong tendency to take on a thermodynamically stable state by crystallite growth accompanied by a reduction in specific surface area.

It has been found that catalyst supports containing silicon dioxide are also subject to such aging. Hydrothermal conditions accelerate aging. It is furthermore known that contaminants, in particular alkali metals, promote the aging of supports containing silicon dioxide under hydrothermal conditions (c.f. for example R. K. Iler in *The Chemistry of Silica,* page 544, John Wiley & Sons (1979)).

It has surprisingly also been found that the catalyst supports based on pyrogenically produced silicon dioxide described in EP 0 393 356 are also subject to aging under hydrothermal conditions, wherein small pores combine to yield larger pores with loss of specific surface area. Initially, pore volume remains virtually unchanged during such aging. This aging is unexpected because the pyrogenic silicon dioxide of which the supports consist has excellent temperature resistance according to investigations with a scanning electron microscope, the morphology of pyrogenic silicon dioxide does not change on heating to temperatures of up to 1000° C. for a period of 7 days (*Schriftenreihe Pigmente Nr.* 11: *Grundlage von AEROSIL®;* Degussa publication, 5th edition, June 1993, page 20).

An object of the present invention is accordingly to provide catalyst supports containing silicon dioxide which exhibit improved aging resistance when used under hydrothermal conditions.

SUMMARY OF THE INVENTION

The above and other objects of this invention are achieved by the use of catalysts which have an active component on a catalyst support containing silicon dioxide, wherein the catalyst support is modified by impregnation with soluble compounds of at least one element from group IVB of the Periodic System of Elements.

The silicon dioxide used in accordance with the present invention may be a natural or synthetic material. Bentonites, such as montmorillonite, may for example be considered as a natural silicon dioxide. Silica gels or precipitated silicas produced by wet chemical methods are suitable synthetic materials. Silicon dioxides produced by flame hydrolysis, so-called pyrogenic silicon dioxides, are preferably used.

BRIEF DESCRIPTION OF DRAWINGS

The present invention will be further understood with regard to the drawings, wherein.

DETAILED DESCRIPTION OF INVENTION

Figure 1:
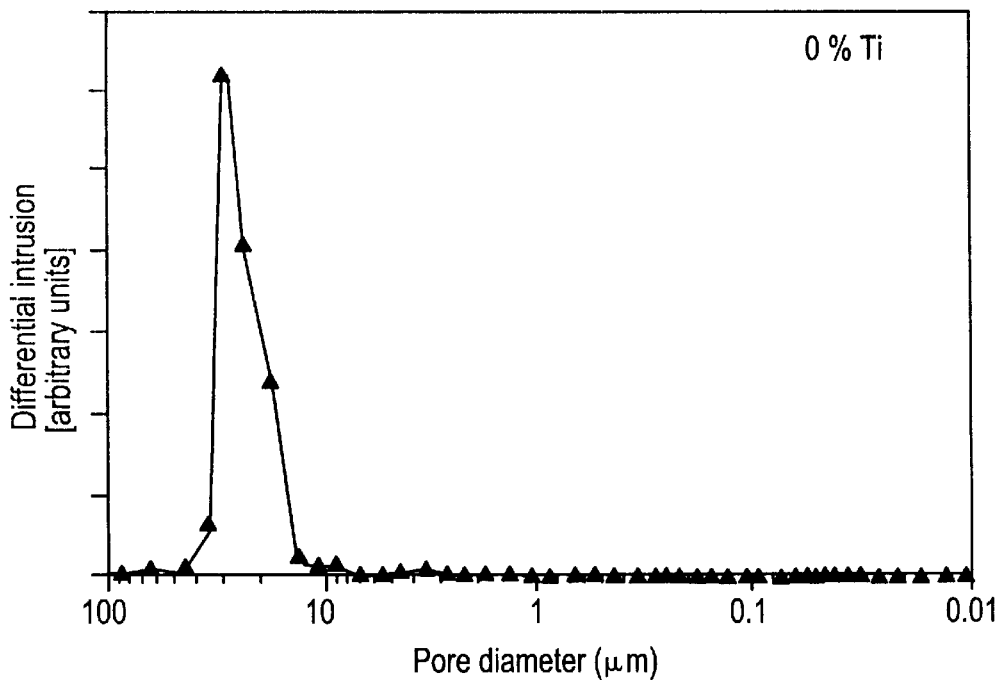
FIG. 1 is a plot of differential intrusion vs. pore diameter for a pore structure of an unstabilized catalyst support after a hydrothermal aging test.

According to a more detailed aspect of the invention, the stated silica materials are processed in a known manner to produce catalyst supports. Suitable supports can be made from pyrogenic silicon dioxide in the manner described, for example, in EP 0 393 356. At external diameters of 2 to 15 mm, they have a specific surface area of 50 to 400 m$^2$/g, a pore volume of 0.6 to 1.3 ml/g and a crush strength of 50 to 150 N. Abrasion is less than 1%. The supports are 99 wt. % silicon dioxide and have a bulk density of between 400 and 500 g/l. They have almost no pores of a diameter below 5 nm. The pore structure of the catalyst supports shaped from the silicon dioxide materials is stabilized by impregnation with soluble compounds of elements of group IVB of the Periodic System of Elements. To this end, the catalyst supports are impregnated with at least one element of group IVB in a quantity of 0.1 to 25, preferably 0.5 to 10 wt. %, relative to the total weight of the support. Adequate stabilization of the pore structure is not achieved at quantities of below 0.1 wt. %. Depending upon the silicon dioxide material used and the hydrothermal conditions applied, it may be necessary to impregnate the catalyst supports with at least 0.5 wt. % or, under more aggressive reaction conditions, with at least 1 wt. %.

The catalyst supports are preferably surface modified with the stabilizing elements using the pore volume impregnation process. This process allows defined loading of the catalyst supports. Other preparation processes may, however, also be used.

Pore volume impregnation is performed by dissolving the soluble compounds of the stabilizing elements in a volume of solvent which is equal to the pore volume of the catalyst supports and then distributing them, for example by spraying, over the supports, which may be rotated in a pill coater during spraying in order to ensure uniform impregnation.

Both aqueous and organic solvents or mixtures thereof may be used for impregnation. Selection of the suitable solvent is dependent upon the stabilizing element compound used. When using titanium(III) chloride ($TiCl_3$) to achieve stabilization with titanium, preferably water is used as the solvent. An organic titanium compound, such as for example tetrabutoxytitanium ($Ti(C_4H_9O)_4$), may also be used instead of titanium(III) chloride. In this case, butanol is a suitable solvent.

After impregnation, the catalyst support is dried, wherein in the case of organic solvents, appropriate precautions must be taken to avoid any explosion hazard. The treated supports may then be calcined at temperatures of between 160 and 900° C.

The catalyst supports as described herein are particularly advantageous for hydrating olefins to produce lower alkanols. Stabilization of the support is, however, also favorable in other catalytic reactions under hydrothermal conditions. For the hydration of olefins, phosphoric acid is introduced into the catalyst support as the active component. To this end, once the support has been stabilized and optionally then calcined, it is immersed in an aqueous solution of phosphoric acid and impregnated therewith. The phosphoric acid solutions used contain 15 to 85 wt. % of phosphoric acid relative to the total weight of the solution.

A principal area of application for the hydration of olefins is the hydration of ethylene to produce ethanol and diethyl ether and the hydration of propylene to produce isopropanol. Known prior art reaction conditions are used for these reactions.

Changes to the pore structure of catalyst supports containing silicon dioxide under hydrothermal conditions are investigated below. Conventional supports are compared with stabilized supports.

Figure 2:
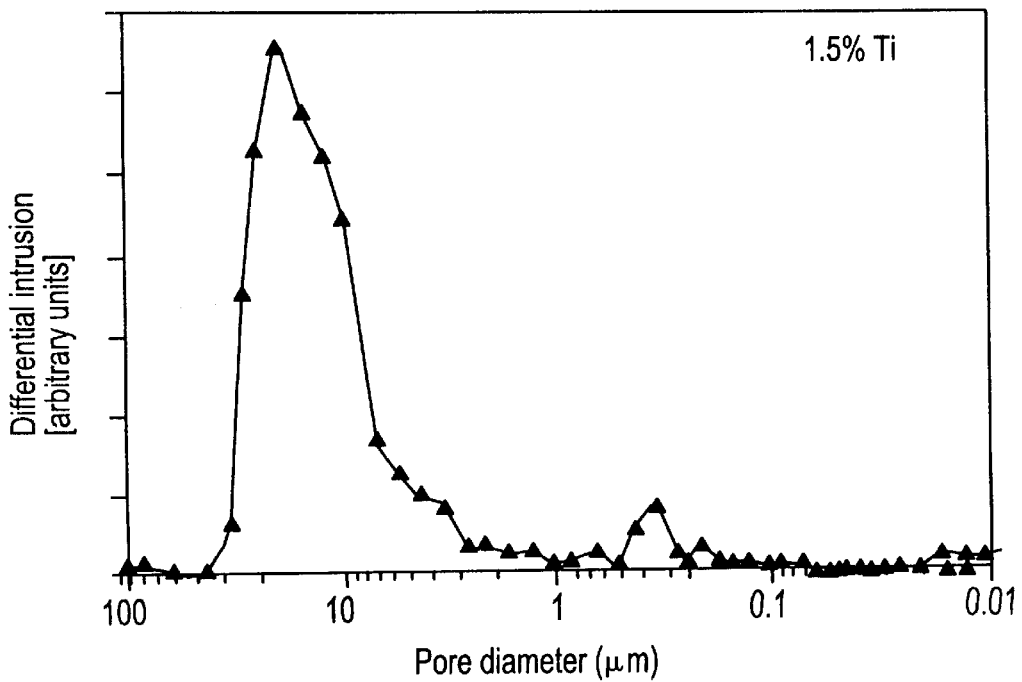
FIG. 2 is a plot of differential intrusion vs. pore diameter for a pore structure of a catalyst support stabilized with 1.5% of titanium after a hydrothermal aging test.
Figure 3:
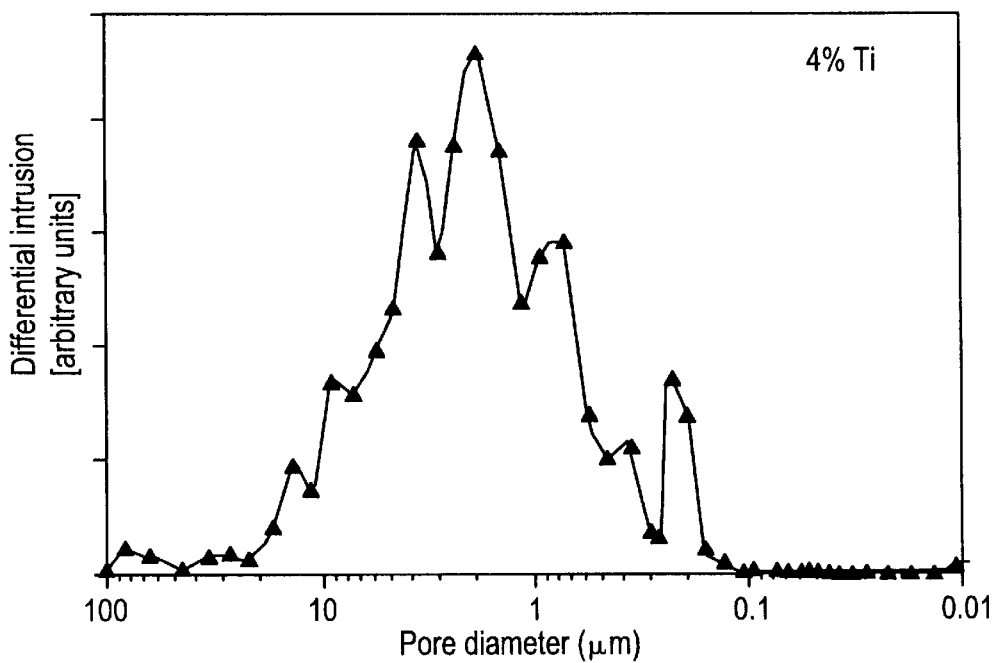
FIG. 3 is a plot of differential intrusion vs. pore diameter for a pore structure of a catalyst support stabilized with 4% of titanium after a hydrothermal aging test.
Figure 4:
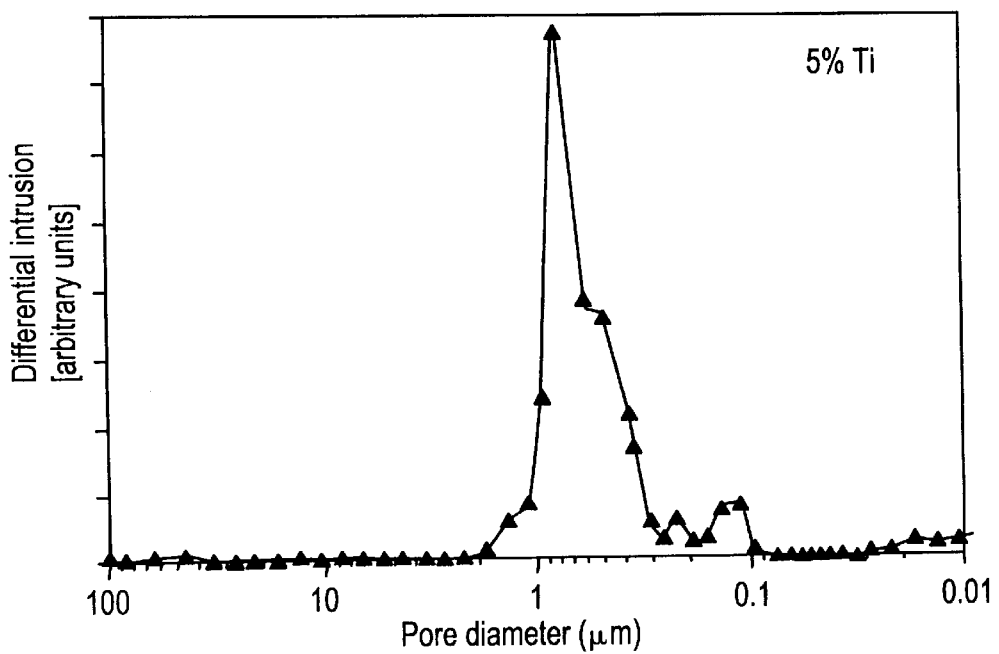
FIG. 4 is a plot of differential intrusion vs. pore diameter for a pore structure of a catalyst support stabilized with 5% of titanium after a hydrothermal aging test.

The pore size distribution curves shown in FIGS. 1 to 4 were determined using known Hg porosimetry methods. They show the differential penetration (intrusion) of the mercury as a function of pore diameter. Arbitrary units were selected for differential intrusion and the curves were each expanded over the available area of the diagram.

Comparative Example 1

A catalyst support made from pyrogenic silica (AEROSIL® Träger 350 from Degussa; specific surface area 180 m²/g; bulk density 490 g/l; total pore volume 0.8 cm³/g; tablets 6 mm in diameter, 5.5 mm in height) was loaded with phosphoric acid (60 wt. %) and heated to 350° C. in a high pressure apparatus at a steam pressure of 15 bar for 41 hours. The pore size distribution of the aged catalyst was determined by Hg porosimetry. The measured pore size distribution is shown graphically in FIG. 1.

The hydrothermally aged supports have a maximum in the pore size distribution at pore diameters of between 20 and 30 μm.

EXAMPLE 1

The above-stated catalyst support was modified with 1.5 wt. % of Ti. In order to modify 100 g of support with 1.5 wt. % of Ti, 33 g of a 15% titanium chloride solution ($TiCl_3$) were diluted with water to 80 ml, corresponding to the pore volume of the support material. The support material was impregnated with this solution.

After 30 minutes' exposure to the solution, the support was dried in a drying cabinet at 100° C. for 3 hours and then calcined in a furnace at 600° C. for a period of 4 hours. The support was then loaded with phosphoric acid (60 wt. %) and left in a high pressure apparatus at a steam pressure of 15 bar at 350° C. for 40 hours. The pore size distribution of the aged catalyst was again determined by Hg porosimetry. The pore size distribution is shown graphically in FIG. 2.

The maximum of the pore size distribution is between 10 and 20 μm. In comparison with the undoped catalyst used in Comparative Example 1, the catalyst doped with 1.5 wt. % of Ti has a higher proportion of small pores of a diameter of below 10 μm after aging.

EXAMPLE 2

A catalyst support as described in Comparative Example 1 was modified with 4 wt. % of Ti. In order to modify 100 g of support with 4 wt. % of Ti, 85.93 g of a 15% titanium chloride solution were diluted with water to 80 ml and distributed over the support to impregnate it.

After 30 minutes' exposure to the solution, the support was dried in a drying cabinet at 100° C. for 3 hours and then calcined in a furnace at 600° C. for a period of 4 hours. The support was then loaded with phosphoric acid (60 wt. %) and left in a high pressure apparatus at a steam pressure of 15 bar at 350° C. for 43 hours. The pore size distribution of the aged catalyst was determined by Hg porosimetry. The pore size distribution is shown graphically in FIG. 3.

The pore size distribution of this specimen is very wide. The maximum of the pore size distribution is approximately 2 μm. In comparison with the undoped catalyst used in Comparative Example 1, the catalyst doped with 4 wt. % of Ti has a very high proportion of pores of a diameter of less than 10 μm. In comparison with the undoped catalyst from Comparative Example 1, the catalyst doped with 4 wt. % of Ti is distinctly more stable and the enlargement of pore diameter is distinctly less marked.

EXAMPLE 3

A catalyst support as described in Comparative Example 1 was modified with 5 wt. % of Ti. In order to modify 100 g of support with 5 wt. % of titanium, 35.5 g of tetrabutoxytitanium ($Ti(C_4H_9O)_4$) were diluted to 80 ml with butanol and distributed over the support.

After 30 minutes' exposure to the solution, the support was dried in a drying cabinet at 100° C. for 3 hours and then calcined in a furnace at 600° C. for a period of 4 hours. The support was then loaded with phosphoric acid and heated to 350° C. in a high pressure apparatus at a steam pressure of 15 bar for 41.5 hours. The pore size distribution of the aged catalyst was determined by Hg porosimetry. The pore size distribution is shown graphically in FIG. 4.

The maximum of the pore size distribution is approximately 0.7 μm. There are virtually no pores of a diameter greater than 3 μm. In comparison with the undoped catalyst from Comparative Example 1, the catalyst doped with 5 wt. % of Ti is distinctly more stable. The average pore diameter for the catalyst doped with 5 wt. % of Ti is smaller by a factor of 35 than in the case of the undoped catalyst from Comparative Example 1.

These Examples clearly demonstrate the very good long term stability of the Ti doped phosphoric acid catalysts based on catalyst supports containing silicon dioxide.

Analysis of the pore volume of the supports showed that hydrothermal aging brought about only insignificant changes in pore volume. All that occurred was that the smaller pores of the fresh support combined to give larger pores, wherein this growth could be slowed down by stabilization. Catalysts based on catalyst supports containing silicon dioxide can advantageously be used for catalytic reactions under hydrothermal conditions Further variations and modifications of the foregoing will be apparent to those skilled in the art and are intended to be encompassed by the claims appended hereto.

German priority application 196 07 494.0 is relied on and incorporated herein by reference.

We claim:

1. A method of hydrating an olefin to produce a lower alkanol, comprising reacting an olefin with water in the presence of a catalyst comprising an active component on a support containing silicon dioxide, said catalyst support consists essentially of pyrogenic silicon dioxide and at least one of zirconium and titanium wherein said pyrogenic silicon dioxide is modified by impregnation with soluble compounds of at least one of zirconium and titanium to thereby obtain said alkanol.

2. The method according to claim 1, wherein said catalyst support is modified with at least one of zirconium and titanium in a quantity of 0.1 to 25 wt. %, relative to the weight of the support.

3. The method according to claim 1, wherein phosphoric acid is the active component.

4. The method according to claim 1 wherein the olefin is ethylene.

5. The method according to claim 1, wherein the olefin is propylene.

6. A method of hydrating an olefin to produce a lower alkanol, comprising reacting an olefin with water in the presence of a catalyst comprising an active component on a support, said catalyst support consisting essentially of silicon dioxide and at least one of zirconium and titanium wherein said silicon dioxide has a purity of at least 99 wt. %, said silicon dioxide being modified by impregnation with soluble compounds of at least one of zirconium and titanium, said modified silicon dioxide being calcined at temperatures from 160–900° C., to thereby obtain said alkanol.

7. The method of hydrating an olefin to produce a lower alkanol as defined in claim 6, wherein said silicon dioxide is pyrogenic silicon dioxide.

8. The method according to claim 6, wherein said catalyst support is modified with at least one of zirconium and titanium in a quantity of 0.1 to 25 wt. %, relative to the weight of the support.

9. The method according to claim 6, wherein phosphoric acid is the active component.

10. The method according to claim 6 wherein the olefin is ethylene.

11. The method according to claim 6, wherein the olefin is propylene.

12. The method according to claim 7, wherein said catalyst support is modified with at least one of zirconium and titanium in a quantity of 0.1 to 25 wt. %, relative to the weight of the support.

13. The method according to claim 7, wherein phosphoric acid is the active component.

14. The method according to claim 7 wherein the olefin is ethylene.

15. The method according to claim 7, wherein the olefin is propylene.

16. A method of hydrating an olefin to produce a lower alkanol, comprising coating a silicon support with a solution of a soluble compound of at least one of zirconium and titanium to form a coated support;

drying and calcining said coated support;

impregnating said coated support with an active component; and reacting an olefin with said active component on said coated support to obtain said alkanol.

* * * * *